(12) United States Patent
Nair et al.

(10) Patent No.: US 7,416,534 B2
(45) Date of Patent: Aug. 26, 2008

(54) MEDICAL DEVICE INCLUDING ACTUATOR

(75) Inventors: Ajitkumar B. Nair, Fremont, CA (US);
Alain F. Sadaka, Los Gatos, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 347 days.

(21) Appl. No.: 10/873,792

(22) Filed: Jun. 22, 2004

(65) Prior Publication Data
US 2005/0283095 A1    Dec. 22, 2005

(51) Int. Cl.
*A61B 5/00* (2006.01)
*A61M 25/00* (2006.01)

(52) U.S. Cl. ............................................ 600/585

(58) Field of Classification Search ................. 600/585, 600/151, 433, 434; 604/95.05
See application file for complete search history.

(56) References Cited

U.S. PATENT DOCUMENTS

| | | | |
|---|---|---|---|
| 3,174,851 A | 3/1965 | Buehler et al. | |
| 3,351,463 A | 11/1967 | Rozner et al. | |
| 4,427,000 A | 1/1984 | Ueda | |
| 4,790,624 A | 12/1988 | Van Hoye et al. | |
| 4,799,474 A | 1/1989 | Ueda | |
| 4,827,941 A | 5/1989 | Taylor et al. | |
| 4,919,133 A | 4/1990 | Chiang | |
| 4,944,727 A | 7/1990 | McCoy | |
| 4,969,709 A | 11/1990 | Sogawa et al. | |
| 4,984,581 A | 1/1991 | Stice | |
| 5,055,101 A | 10/1991 | McCoy | |
| 5,114,402 A * | 5/1992 | McCoy ................. | 604/95.05 |
| 5,135,517 A * | 8/1992 | McCoy ................. | 604/531 |
| 5,238,005 A | 8/1993 | Imran | |
| 5,243,996 A | 9/1993 | Hall | |
| 5,341,818 A | 8/1994 | Abrams et al. | |
| 5,349,964 A | 9/1994 | Imran et al. | |
| 5,368,049 A | 11/1994 | Raman et al. | |
| 5,433,200 A | 7/1995 | Fleischhacker, Jr. | |
| 5,524,434 A | 6/1996 | Ma | |
| 5,594,330 A | 1/1997 | Jacobsen | |
| 5,744,947 A | 4/1998 | Jacobsen et al. | |
| 5,747,692 A | 5/1998 | Jacobsen et al. | |
| 5,747,993 A | 5/1998 | Jacobsen et al. | |
| 5,769,389 A | 6/1998 | Jacobsen et al. | |

(Continued)

FOREIGN PATENT DOCUMENTS

JP    7328127    12/1995

(Continued)

*Primary Examiner*—Max Hindenburg
*Assistant Examiner*—Jonathan M Foreman
(74) *Attorney, Agent, or Firm*—Crompton, Seager & Tufte, LLC

(57) ABSTRACT

An actuating medical device and methods for making and using the same. The actuating medical device may include a proximal shaft portion having a distal end region, an actuating shaft portion attached to the distal end region, one or more actuating members coupled to or otherwise disposed adjacent the actuating shaft portion, and a distal shaft portion attached to the actuating shaft portion. The actuating shaft portion may include a shape memory material and may be adapted to shift between a first configuration and a second configuration. Using the actuating medical device may include positioning the actuating medical device in a blood vessel and shifting the actuating shaft portion between the first and second configurations.

34 Claims, 12 Drawing Sheets

U.S. PATENT DOCUMENTS

| | | | |
|---|---|---|---|
| 5,769,796 | A | 6/1998 | Palermo et al. |
| 5,771,902 | A | 6/1998 | Lee et al. |
| 5,772,609 | A | 6/1998 | Nguyen et al. |
| 5,813,997 | A | 9/1998 | Imran et al. |
| 5,885,258 | A | 3/1999 | Sachdeva et al. |
| 5,932,035 | A * | 8/1999 | Koger et al. ................ 148/563 |
| 5,933,002 | A | 8/1999 | Jacobsen et al. |
| 5,938,623 | A * | 8/1999 | Quiachon et al. ........... 600/585 |
| 6,139,510 | A | 10/2000 | Palermo |
| 6,183,432 | B1 * | 2/2001 | Milo ........................... 604/22 |
| 6,254,550 | B1 * | 7/2001 | McNamara et al. ......... 600/585 |
| 6,306,105 | B1 * | 10/2001 | Rooney et al. ............... 600/585 |
| 6,329,069 | B1 | 12/2001 | Azizi et al. |
| 6,508,803 | B1 | 1/2003 | Horikawa et al. |
| 6,514,217 | B1 | 2/2003 | Selmon et al. |
| 6,531,861 | B1 | 3/2003 | Jacobsen et al. |
| 6,592,570 | B2 | 7/2003 | Abrams et al. |
| 2001/0000041 | A1 | 3/2001 | Selmon et al. |
| 2001/0031963 | A1 * | 10/2001 | Sharkey et al. ................ 606/41 |
| 2003/0009146 | A1 * | 1/2003 | Muni et al. .................. 604/500 |
| 2003/0069520 | A1 | 4/2003 | Skujins et al. |
| 2003/0069521 | A1 | 4/2003 | Reynolds et al. |
| 2003/0097080 | A1 | 5/2003 | Esashi et al. |
| 2003/0191492 | A1 | 10/2003 | Gellman et al. |
| 2003/0199818 | A1 | 10/2003 | Waldhauser et al. |
| 2004/0073141 | A1 * | 4/2004 | Hartley et al. ................ 600/585 |
| 2004/0167442 | A1 | 8/2004 | Shireman et al. |
| 2005/0038358 | A1 * | 2/2005 | Furukawa ................... 600/585 |

FOREIGN PATENT DOCUMENTS

WO    WO 02/00286    1/2002

* cited by examiner

MEDICAL DEVICE INCLUDING ACTUATOR

FIELD OF THE INVENTION

The invention relates to intracorporal medical devices, for example, intravascular medical devices. More particularly, the invention relates to intracorporal medical devices that include an actuating section or portion including shape memory materials, which may have desirable moving, shifting, and bending characteristics.

BACKGROUND

A wide variety of intracorporal medical devices have been developed for medical use, for example, intravascular use. Some of these devices include guidewires and other such devices that have certain actuating and/or bending characteristics. Of the known intracorporal medical devices, each has certain advantages and disadvantages. There is an ongoing need to provide alternative designs and methods of making and using medical devices with desirable actuating and/or bending characteristics.

BRIEF SUMMARY

The invention provides design, material, and manufacturing method alternatives for intracorporal medical devices having actuating and/or bending characteristics. In at least some embodiments, the medical devices include an elongate shaft having a proximal shaft portion, an actuating shaft portion attached to the proximal shaft portion, one or more actuating members coupled to or otherwise disposed adjacent the actuating shaft portion, and a distal shaft portion attached to the actuating shaft portion. The actuating shaft portion may include a shape memory material and may be adapted to shift between a first configuration and a second configuration. For example, the actuating shaft portion may shift between a generally lengthened and a generally shortened configuration or the actuating shaft portion may shift between a curved and a generally straightened configuration. In some embodiments, the actuating shaft portion can be shifted from one configuration to another by heating or otherwise activating the actuating shaft portion. In addition, the actuating members may be configured to bias the actuating shaft portion into one of the two configurations. Some of these as well as some other features and characteristics are described in more detail below.

Methods for making and using medical devices are also disclosed. For example, methods for making an intracorporal medical device may include providing an elongate shaft including a proximal shaft portion, an actuating shaft portion attached to the proximal shaft portion, and a distal shaft portion attached to the actuating shaft portion and attaching one or more actuating members adjacent to the actuating shaft portion. Methods for using these medical devices may include positioning the actuating medical device in a blood vessel and shifting the actuating shaft portion between the first and second configurations. Some further details regarding these and other methods are described in more detail below.

The above summary of some embodiments is not intended to describe each disclosed embodiment or every implementation of the present invention. The Figures, and Detailed Description, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

Figure 1:
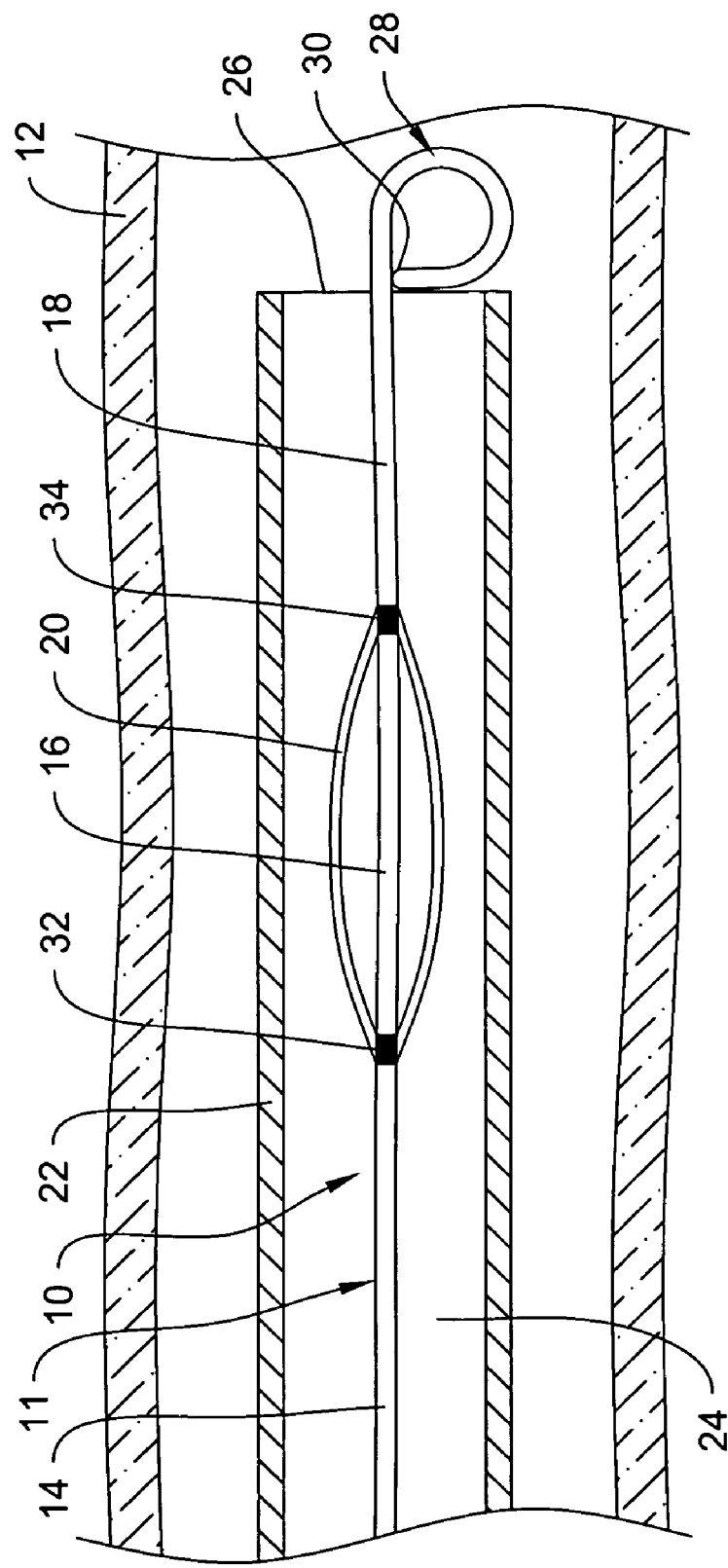
FIG. 1 is a partial cross-sectional side view of an example medical device disposed in catheter within a blood vessel.

FIG. 1 is partial cross-sectional side view of an example actuating medical device 10 disposed in a blood vessel 12. Medical device 10 may include an elongate shaft 11 including a proximal shaft portion 14, an actuating shaft portion 16, and a distal shaft portion 18. One or more actuators or actuating members 20 may be coupled to device 10, for example, adjacent actuating shaft portion 16.

Figure 2:
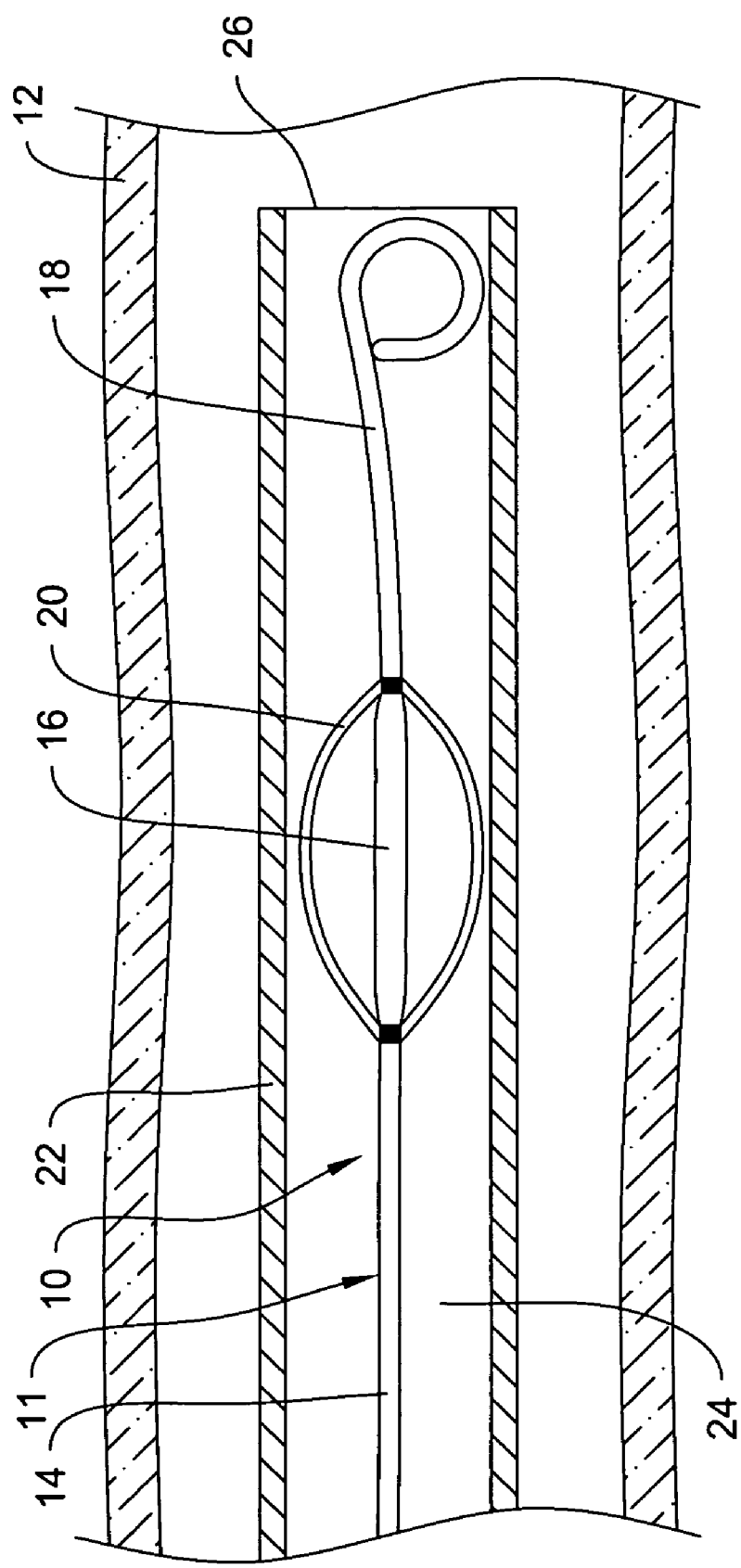
FIG. 2 is a partial cross-sectional side view of the device shown in FIG. 1, where the actuating shaft has shifted configurations.

In at least some embodiments, actuating shaft portion 16 includes a shape memory material and is adapted to shift between a first configuration and a second configuration. For example, the first configuration may be a generally elongated configuration as shown in FIG. 1. The second configuration may be characterized by actuating shaft portion 16 being shortened as shown in FIG. 2. On the other hand, the different configurations may include those where actuating shaft portion 16 is shortened when in the first configuration and then elongated when in the second configuration. Alternatively, the different configuration may be typified by actuating shaft portion 16 being straightened, curved, spiral in shape, or in any other suitable configuration. The ability to change the configuration of actuating shaft portion 16 may desirably impact the navigation ability and/or trackability of medical device 10 as well as improve the ability of device 10 and/or other devices used with it to carry out their desired function such as diagnosis, treatment, drug delivery, and the like. Shifting may be controlled selectively or in any other suitable manner. For example, shifting may be induced by changing the temperature of actuating shaft portion 16. Temperature change may be achieved, for example, by passing current through shaft 11 and into actuating shaft portion 16 so that it heats up, or other such techniques.

Actuating members 20 may be adapted to bias actuating shaft portion 16 into one configuration by exerting a force on actuating shaft portion 16. For example, actuating members 20 may bias actuating shaft portion 16 into a first elongated configuration by exerting a pushing, pulling, or elongating force onto actuating shaft portion 16. Alternatively, actuating members 20 may bias actuating shaft portion 16 into a first shortened configuration by exerting a pushing, pulling, or shortening force onto actuating shaft portion 16. Regardless of which arrangement is utilized, this feature allows actuating shaft portion 16 to remain or be held in the one configuration and then be shifted to another when "stimulated", heated, or activated. Upon activation of actuating shaft portion 16, actuating shaft portion 16 may overcome the bias of actuating members 20 and shift into the other configuration. For example, actuating shaft portion 16 may be made from a shape memory material that can return to a pre-set shape (with sufficient force to overcome the biasing force exerted by actuating members 20) when exposed to particular thermal conditions. When the activating stimulus is removed or otherwise allowed to dissipate from actuating shaft portion 16, actuating members 20 can shift actuating shaft portion 16 back toward the first configuration. Some additional details of this feature are described in more detail below.

The ability to selectively control the configuration of actuating shaft portion 16 may be desirable for a number of interventions and/or uses for medical device 10. For example, the actuating action of device 10 may be useful for clearing the distal end of a catheter, for example, a microcatheter 22. According to this embodiment, device 10 (with actuating shaft portion 16 in the first configuration) can be advanced through a lumen 24 defined within microcatheter 22 to a position adjacent a distal opening 26 or positioned just outside opening 26 as seen in FIG. 1. Actuating shaft portion 16 can then be activated so that it shifts to the shortened configuration as shown in FIG. 2. The reverse set of configurations can also be utilized where distal shaft portion 18 is positioned adjacent opening 26 and actuating shaft portion 16 is activated so as to shift from the shortened to the elongated configuration. This shifting mechanism can help clear debris that might otherwise collect adjacent opening 26. Moreover, a user can repeatedly stimulate and the remove the stimulus from actuating shaft portion 16 so that actuating shaft portion 16 oscillates back-and-forth through opening 26. This feature would be useful for clearing debris and keeping opening 26 clear from debris.

Actuating shaft portion 16 may also give device 10 a number of additional desirable features. For example, the ability to shift configurations may be used to curve and/or straighten device 10. This feature, which is described in more detail below, may improve the trackability and/or navigational abilities of device 10 through the tortuous vasculature. In addition, because of the improved navigational abilities of device 10, other interventions may be more easily performed such as catheterization, drug and/or stent delivery, angioplasty, etc.

Actuating shaft portion 16 may be made from and/or include a number of different materials including shape memory materials. Shape memory materials are those that can revert to or otherwise "remember" a pre-set shape when exposed to the appropriate thermal conditions. Shape memory materials exist in two different temperature-dependent phases or crystalline structures. The lower temperature crystalline structure is called martensite, which tends to be softer, more ductile, and easily deformed. The higher temperature crystalline structure is called austenite, which tends to be harder and less flaccid. When a martensitic shape memory material is heated, it transforms into austenite occurs over a range of temperatures beginning with the austenite starting temperature ($A_s$) and ending with the austenite finishing temperature ($A_f$). Similarly, austenite that is cooled transforms to martensite over a range of temperatures starting with the martensite starting temperature ($M_s$) and ending with the martensite finishing temperature ($M_f$). A temperature hysteresis exists for these transformations characterized by the fact that the temperature range for the martensite-to-austenite transformation is generally higher than the austenite-to-martensite transformation.

Setting the shape of a shape memory material can be achieved using any process known in the art. For example, in some embodiments, setting the shape of a shape memory material can be achieved by constraining the material into the desired shape, heating the material to a temperature above (often well above) $A_f$ (often in the range of about 250-650° C. or so), and then allowing the material to cool. The result is a temperature-dependent structure that can be freely deformed into a wide variety of shapes (while in the martensite form) and then forcefully revert back to the pre-set shape by simply heating the material above its activation or transformation temperature (e.g., $A_f$). The transformation temperature for a particular shape memory material can vary depending on the composition of the particular shape memory material as well as the parameters of the heat treatment. For example, an activation or transformation temperature can be defined in the range of about −100° C. to about 100° C. or so, which may be suitable for use with shape memory materials included with actuating shaft portion 16. In some embodiments, actuating shaft portion 16 can include a shape memory material with an activation temperature that is near or slightly above body temperature (e.g., about 35° C. to about 42° C. or so). A number of other temperatures are also contemplated.

The shape memory effect can be described as being "one-way" or "two-way". One-way shape memory is similar to what is described above and is characterized by the shape memory material being able to recover a preset shape upon heating above the transformation temperature. Two-way shape memory is similar to one-way shape memory except that two-way shape memory materials not only revert to a preset shape upon heating but also revert to an alternative pre-set shape upon cooling. Imparting two-way shape memory can be achieved using any process known in the art. In some embodiments, for example, two-way shape memory can be imparted by providing a shape memory material that has already been programmed with one-way shape memory, and cooling it below $M_f$ and then deforming it into a desired second shape. The material is then heated above $A_f$ and allowed to revert to the preset austenite shape. This process is repeated many times (i.e., about 20-30 times) until the desired two-way shape memory is achieved.

In some embodiments, actuating shaft portion 16 may include a shape memory material such as nitinol. The word nitinol was coined by a group of researchers at the United States Naval Ordinance Laboratory (NOL) who were the first to observe the shape memory behavior of this material. The word nitinol is an acronym including the chemical symbol for nickel (Ni), the chemical symbol for titanium (Ti), and an acronym identifying the Naval Ordinance Laboratory (NOL). In some embodiments, nitinol alloys can include in the range of about 50 to about 60 weight percent nickel, with the remainder being essentially titanium. It should be understood, however, that in other embodiments, the range of weight percent nickel and titanium, and or other trace elements may vary from these ranges. Within the family of commercially available nitinol alloys, are categories designated as "superelastic" (i.e. pseudoelastic) and "linear elastic" which, although similar in chemistry, exhibits distinct and useful mechanical properties.

Superelastic alloys typically display a substantial "superelastic plateau" or "flag region" in its stress/strain curve. Such alloys can be desirable in some embodiments because a suitable superelastic alloy will provide a portion of device 10 (e.g., actuating shaft portion 16) that exhibits some enhanced ability, relative to some other non-superelastic materials, of substantially recovering its shape without significant plastic deformation, upon the application and release of stress, for example, during placement of the catheter in the body.

As stated above, in some embodiments, actuating shaft portion 16 can be formed of a shape-memory material, for example a shape memory alloy. In such embodiments, the shape memory effect can be used in the shifting of actuating shaft portion 16 from the first configuration to the second configuration. For example, in some embodiments, actuating shaft portion 16 can include or be made of a shape memory alloy that is martensite at body temperature, and has a final austenite transition temperature ($A_f$) somewhere in the temperature range above body temperature. This feature allows actuating shaft portion 16 to be advanced through a blood vessel (or a suitable microcatheter) while in a martensitic state, and maintain a martensitic state until exposed to a temperature higher than body temperature. For example, in some such embodiments, the shape memory alloy has a final austenite transition temperature in the range of about 37° C. and about 45° C. In some such embodiments, it may be desirable that the final austenite transition temperature be at least slightly above body temperature, to ensure there is not final transition at body temperature. Actuating shaft portion 16 can be heated to the necessary temperature above body temperature to make the transformation from martensite to austenite using an external heating means or mechanism. Such mechanisms may include the injection of heated fluid through the microcatheter, the use of electrical or other energy to heat the actuating shaft portion 16, or other such techniques.

In other example embodiments, actuating shaft portion 16 can include or be made of a shape memory alloy that could have a transition temperature $M_d$ (wherein $M_d$=highest temperature to stress-induce martensite) that is in the range of body temperature (e.g. 37° C.) or greater, below which the alloy retains sufficient stress-induced martensitic property to allow placement of actuating shaft portion 16 at or above its final austenite transition temperature ($A_f$). In other words, this allows actuating shaft portion 16 to be carried while constrained in a stress-induced martensitic (SIM) state, and recover its preformed, austenitic shape when released from the constraints, at a temperature that may be substantially above the final austenite transition temperature without significant plastic, or otherwise permanent deformation. In this embodiment, the final austenite temperature may be quite low, e.g., 4° C. or lower, or it may be up to room temperature or higher. In yet other embodiments, the transition temperature may be near or slightly below body temperature.

Some examples of Nitinol cylinders having desired transition temperatures, as noted above, can be prepared according to known methods. For example, actuating shaft portion 16 can be arranged in the second configuration (e.g., shortened or expanded, depending on the desired transition) and heated to a temperature above the transition temperature. Actuating shaft portion 16 is then subjected to thermoelastic martensitic transformation (e.g., as described in U.S. Pat. No. 5,190,546 incorporated by reference in its entirety herein) by cooling below the transition temperature range of the alloy. The transition temperature can be modified by varying the ratios of each metal in the alloy and in one embodiment, for example, is within the range between about 25° C. to 45° C. at which actuating shaft portion 16 shifts. Nitinol cylinders having a martensite temperature $M_d$ below which the alloy can assume a stress-induced martensitic condition while being stressed to the extent necessary to place or otherwise use the device, of greater than about 37° C., or in some embodiments, greater than about 40° C., are also prepared according to known methods, e.g., U.S. Pat. No. 4,505,767. One example alloy would act, at about 37° C., as a constant force spring over a strain range up to about 5% or more. This is a measurement of the degree to which an alloy, at a given temperature, can be strained in a purely austenitic state by the formation of stress-induced martensite without significant plastic deformation. In other words, the strain caused by the application of a given stress at a given temperature is substantially recoverable. In practice, the maximum stress realized occurs sometime during the process of placing a nitinol device at a given temperature. Accordingly, a suitable alloy will provide a device that is capable of substantially recovering its austenitic shape without significant plastic deformation, upon placement of actuating shaft portion 16 in the body.

It can be appreciated that this shape memory characteristic can be utilized in order to provide the desired characteristics to device 10. For example, the first configuration of actuating shaft portion 16 may be the martensite form of nitinol. This material can be held or biased in the desired shape configuration by actuating members 20 (such as either of those seen in FIG. 1 or 2). Activating actuating shaft portion 16 can occur, for example, by passing current through device 10 so as to heat actuating shaft portion 16 above its activation temperature and causing actuating shaft portion 16 to transform into the second configuration. The second configuration may be the austenite form of nitinol that is pre-set to the desired shape. The second configuration can be either elongated (as seen in FIG. 1) or shortened (and/or fattened as seen in FIG. 2). Hence, actuating shaft portion 16 can be positioned within a blood vessel in the first configuration (i.e., either "short" or "long") and then heated so that it shifts to the second configuration (i.e., either from "short" to "long" or from "long" to "short") according to the one-way shape memory effect as described above. The transformation may be set to occur at a temperature near body temperature, for example, in the range of about 32° C. to about 42° C., or so. Other temperatures are also contemplated. In addition, actuating shaft portion 16 can have two-way shape memory (as described above) so that it shifts from the first configuration to the second configuration upon heating and from the second configuration back to the first configuration (or some other configuration) upon cooling.

Generally, actuating shaft portion 16 includes a shape memory material that can exhibit shape memory effects as described above. For example, actuating shaft portion 16 may include nitinol. Actuating shaft portion 16, however, is not intended to being limited to solely shape memory nitinol as other materials can be used including any of those materials described herein. Additionally, actuating shaft portion 16 need not be made only from shape memory materials. For example, actuating shaft portion 16 may include other materials (in addition to a shape material) such as other metals, metal alloys, polymers, and the like.

Actuating members 20 are configured to apply a force onto actuating shaft portion 16 so as to hold it in one of the configurations. For example, actuating members 20 may exert a force onto actuating shaft portion 16 so that it remains "elongated" (or "shortened") when not heated. As described above, heating causes actuating shaft portion 16 to shift to the second configuration. The properties of shape memory materials allow the above-mentioned transformation to occur with sufficient force so as to overcome the biasing force of actuating members 20. As described above, removing the current allows actuating shaft portion 16 to cool—thus, allowing actuating members 20 to return actuating shaft portion 16 back to the first configuration. The current can be pulsed or otherwise tuned in a manner that allows actuating shaft portion 16 to oscillate between the shortened and the elongated configurations. It should be noted that a number of alternative shape configurations are contemplated such as straightened, curved, etc. that can analogously fit into the general scheme described above.

Proximal shaft portion 14, actuating shaft portion 16, and distal shaft portion 18 may have any one of a number of different shapes, sizes, lengths, arrangements, configurations, etc. For example, the entire elongated shaft 11 including proximal shaft portion 14, actuating shaft portion 16, and distal shaft portion 18 may include structure and/or components found in any typical guidewire configuration. For example, proximal shaft portion 14 may be a typical intravascular guidewire shaft, or the like, or any other suitable shaft. According to this embodiment, proximal shaft portion 14 may include any of the structural characteristics typically known in the relevant art. Likewise, actuating shaft portion 16 may be inserted into a guidewire or other suitable structure that is defined by proximal shaft portion 14 and distal shaft portion 18. For example, a guidewire may be segmented into proximal shaft portion 14 and distal shaft portion 18, and actuating shaft portion 16 can be disposed therebetween. According to this embodiment, a first connection point 32 may be defined between proximal shaft portion 14 and actuating shaft portion 16, and a second connection point 34 may be defined between actuating shaft portion 16 and distal shaft portion 18. Connection points 32/34 may be any suitable connecting means such a mechanical bond or connector, thermal bond, welding, brazing, adhesive, and the like, or any other suitable type of connection.

Distal shaft portion 18 can also be a guidewire, guidewire segment, and the like, or any other suitable shaft. In some embodiments, distal shaft portion 18 may include additional structures and/or be formed into a desired shape, depending upon the desired functionality of device 10. For example, distal shaft portion 18 may include a distal loop or ring 28. Distal ring 28 may be useful, for example, by increasing the area (i.e., defining a larger section) of device 10 that can be used to clear opening 26 of microcatheter 22. Distal ring 28 may be defined or formed in any suitable manner. For example, distal ring 28 may be formed by curving a distal end 30 of distal shaft portion 18 toward a more proximal position of distal shaft portion 18. Generally, the shape of distal ring 28 may be circular or oval. However, it can be appreciated that distal ring 28 could have any shape including essentially all two and three dimensional shapes. In some embodiments, the various portions of shaft 11 may include other structures such as coils, marker bands, safety/shaping ribbons or wire, various alternative tip constructions, or the like, many of which are known. Some additional features, characteristics, and alternative designs for guidewire constructions (i.e., tip or distal constructions) are disclosed in U.S. patent application Ser. Nos. 10/376,068 filed Feb. 26, 2003; 09/972,276 filed on Oct. 5, 2001; and 10/086,992 filed on Feb. 28, 2002, the entire disclosures of which are herein incorporated by reference.

Actuating members 20 may vary in number, shape, position, and material composition. In general, actuating members 20 may be configured so as to provide the desired amount of biasing force to hold and/or bias actuating shaft portion 16 in a particular configuration, for example, the first configuration. This may be accomplished using 1, 2, 3, 4, 5, 6, or more actuating members 20 having any shape that are positioned anywhere appropriate for holding actuating shaft portion 16 in the desired configuration. For example, device 10 may include a pair of actuating members 20 shaped as wires that are connected adjacent opposite ends of actuating shaft portion 16. These actuating members 20 may be disposed along the exterior of actuating shaft portion 16. In some embodiments, actuating members 20 are distinct structural elements that connect to device 10 adjacent connection points 32/34. According to this embodiment, the opposite ends of actuating members 20 can be attached to the opposite ends of actuating shaft portion and/or connection points 32/34. This allows actuating members 20 to exert a force onto actuating shaft portion 16. For example, actuating members 20 may comprise a wire or spring that exerts a spring force sufficient to elongate or shorten actuating shaft portion 16, depending on whether heating shortens or elongates actuating shaft portion 16. Alternatively, actuating members 20 can be embedded within or more tightly associated with actuating shaft portion 16. In some embodiments, actuating members 20 can be directly attached along the length of actuating shaft portion 16. Examples of some of the other alternatives for actuating members 20 are described in more detail below.

Any portion of device 10 such as proximal shaft portion 14, actuating shaft portion 16, distal shaft portion 18, and actuating members 20 may be made from any suitable materials such as metals, polymers, metal-polymer composites, and the like, or any other suitable materials. Generally, the material composition of actuating members 20 is designed to be sufficiently stiff so as to be able to bias actuating shaft portion 16 into a particular shape configuration. Some examples of suitable metals and metal alloys include stainless steel, such as 304V, 304L, and 316LV stainless steel; mild steel; nickel-titanium alloy such as linear-elastic or super-elastic nitinol, nickel-chromium alloy, nickel-chromium-iron alloy, cobalt alloy, tungsten or tungsten alloys, MP35-N (having a composition of about 35% Ni, 35% Co, 20% Cr, 9.75% Mo, a maximum 1% Fe, a maximum 1% Ti, a maximum 0.25% C, a maximum 0.15% Mn, and a maximum 0.15% Si), hastelloy, monel 400, inconel 825, or the like; other Co—Cr alloys; platinum enriched stainless steel; or other suitable material. In some embodiments, actuating members 20 may be made from a stretchable material such as music wire that may or may not include nitinol.

Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polybutylene terephthalate (PBT), polyether block ester, polyurethane, polypropylene (PP), polyvinylchloride (PVC), polyether-ester (for example a polyether-ester elastomer such as ARNITEL® available from DSM Engineering Plastics), polyester (for example a polyester elastomer such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), silicones, polyethylene (PE), Marlex high-density polyethylene, Marlex low-density polyethylene, linear low density polyethylene (for example REXELL®), polyethylene terephthalate (PET), polyetheretherketone (PEEK), polyimide (PI), polyetherimide (PEI), polyphenylene sulfide (PPS), polyphenylene oxide (PPO), polysulfone, nylon, perfluoro(propyl vinyl ether) (PFA), biocompatible polymers, other suitable materials, or mixtures, combinations, copolymers thereof, polymer/metal composites, and the like. In some embodiments any portion of device 10 can be blended with a liquid crystal polymer (LCP). For example, the mixture can contain up to about 5% LCP.

In some examples, the materials, structures and/or placement/attachment of the actuating members 20 to the shaft may include those that are sufficient to exert a suitable amount of force onto the actuating portion 16 to maintain it in the desired position, while also allowing the shape memory effect to overcome the force when desired. The amount of force may vary depending on the intended use and the material composition of the various components of device 10.

In some embodiments, a coating, for example a lubricious, a hydrophilic, a protective, or other type of coating may be applied over portions or all of device 10. Hydrophobic coatings such as fluoropolymers provide a dry lubricity which improves device handling and exchanges. Lubricious coatings improve steerability and improve lesion crossing capability. Suitable lubricious polymers are well known in the art and may include silicone and the like, hydrophilic polymers such as highdensity polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference.

Any portion of device 10 may also be doped with or otherwise include a radiopaque material. Radiopaque materials are understood to be materials capable of producing a relatively bright image on a fluoroscopy screen or another imaging technique during a medical procedure. This relatively bright image aids the user of device 10 in determining its location. Some examples of radiopaque materials can include, but are not limited to, gold, platinum, palladium, tantalum, tungsten alloy, plastic material loaded with a radiopaque filler, and the like.

In some embodiments, portions of device 10 may also include a degree of MRI compatibility. For example, to enhance compatibility with Magnetic Resonance Imaging (MRI) machines, it may be desirable to make the portions of device 10 in a manner that would impart a degree of MRI compatibility. For example, device 10 or portions thereof may be made of a material that does not substantially distort the image and create substantial artifacts (artifacts are gaps in the image). Certain ferromagnetic materials, for example, may not be suitable because they may create artifacts in an MRI image. Device 10, or portions thereof, may also be made from a material that the MRI machine can image. Some materials that exhibit these characteristics include, for example, tungsten, Elgiloy, MP35N, nitinol, and the like, and others.

Figure 3:
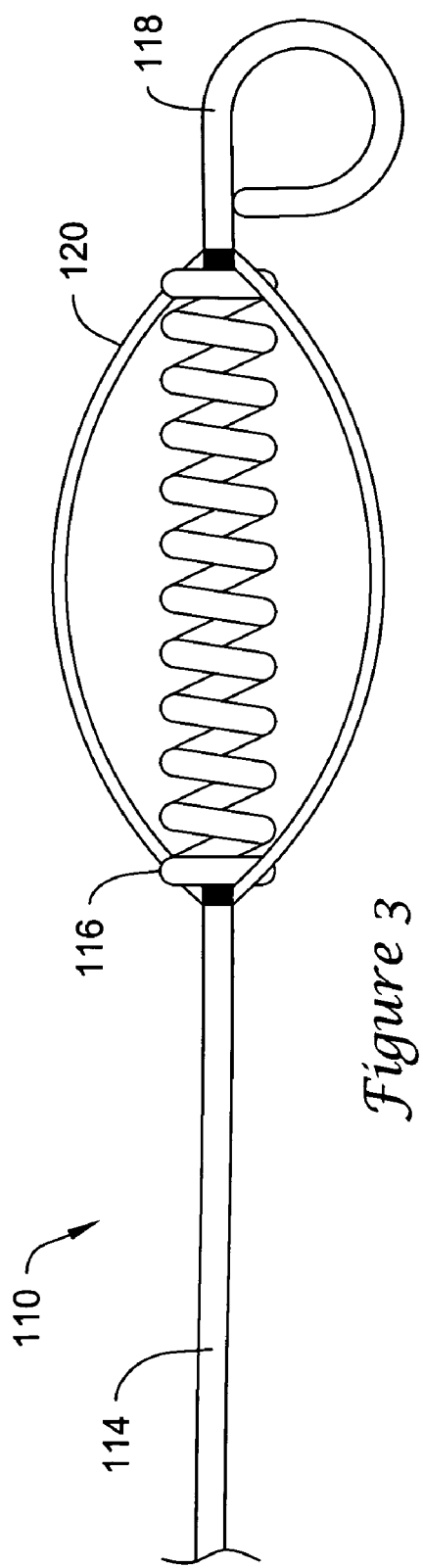
FIG. 3 is a side view of another example medical device.
Figure 4:
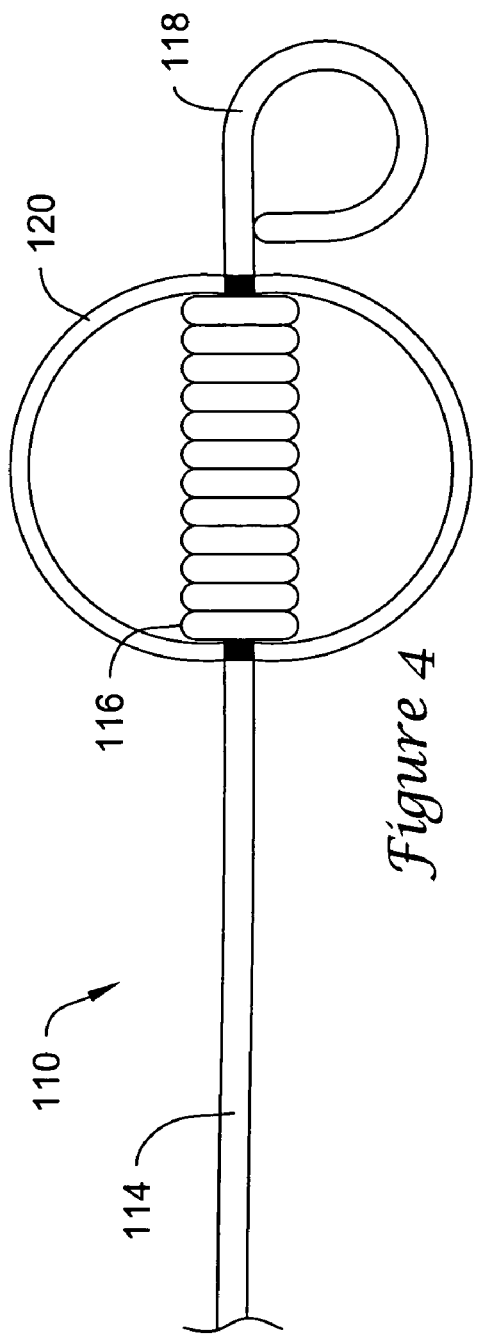
FIG. 4 is a side view of the device shown in FIG. 3, where the actuating shaft is in an alternative shape configuration.

FIG. 3 illustrates an alternative actuating medical device 110 that is similar to any of other devices disclosed herein except that actuating shaft portion 116 has a helical or coiled shape, much like a spring. Just like the earlier embodiment, actuating shaft portion 116 includes a shape memory material and may be disposed between proximal shaft portion 114 and distal shaft portion 118. In addition, device 110 may include one or more actuating members 120 that are configured to bias actuating shaft portion 116 into a particular configuration. For example, actuating members 120 may be configured to generate a sufficient spring tension and/or biasing force that can hold actuating shaft portion 116 in an elongated configuration as seen in FIG. 3. In other embodiments, actuating members 120 may bias actuating shaft portion 116 in a shortened or any other configuration. Activation of actuating shaft portion 116, for example, by passing current through device 110 so that actuating shaft portion 116 heats above the activation temperature, causes actuating shaft portion 116 to return to a previously-set shortened shape, for example, as seen in FIG. 4 if the biased configuration is elongated, or as seen in FIG. 3 if the biased configuration is shortened, or to any other previously-set configuration. These figures illustrate just one of the many available alternative configurations for actuating shaft portion 116 that are contemplated.

Figure 5:
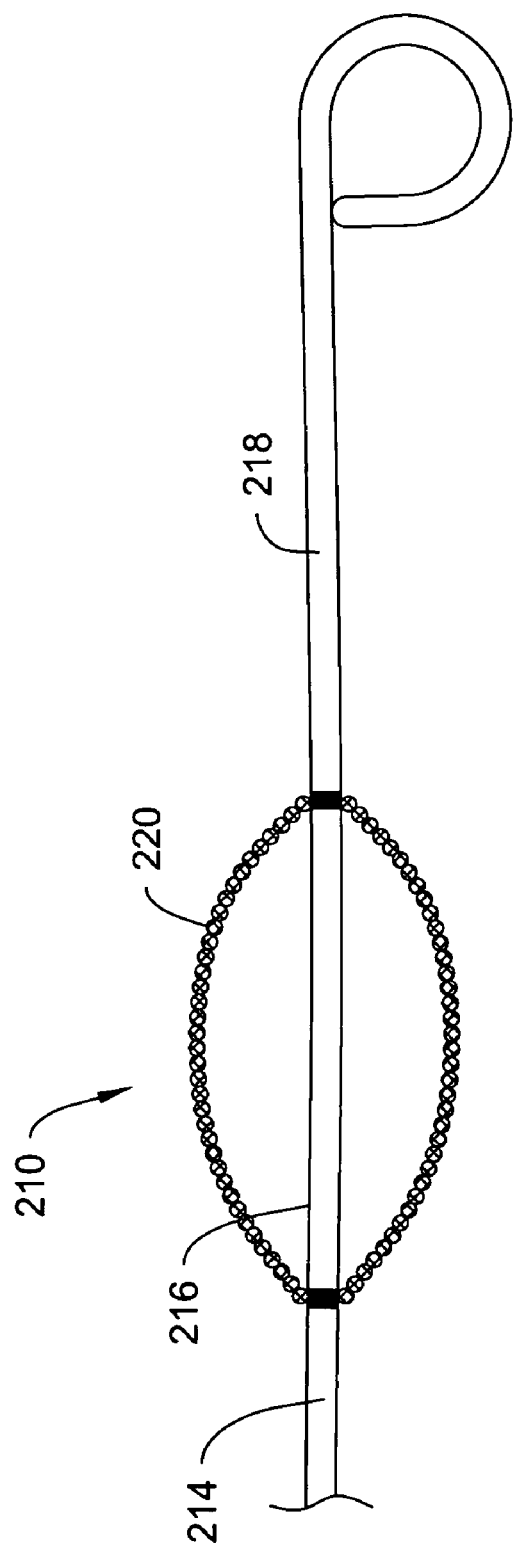
FIG. 5 is a side view of another example medical device.

One of the alternative configurations for the actuating member or members is shown in FIG. 5. Here another example device 210 is shown that has proximal shaft portion 214, actuating shaft portion 216, and distal shaft portion 218. Actuating member 220, however, takes the form of a coil, helix, or spring. It can be easily appreciated how a spring-like actuating member 220 could exert a biasing force or spring tension onto actuating shaft portion 216. Activation of actuating shaft portion 216 can cause it to return to the pre-set shape, overcoming the biasing force of actuating member 220.

Figure 5A:
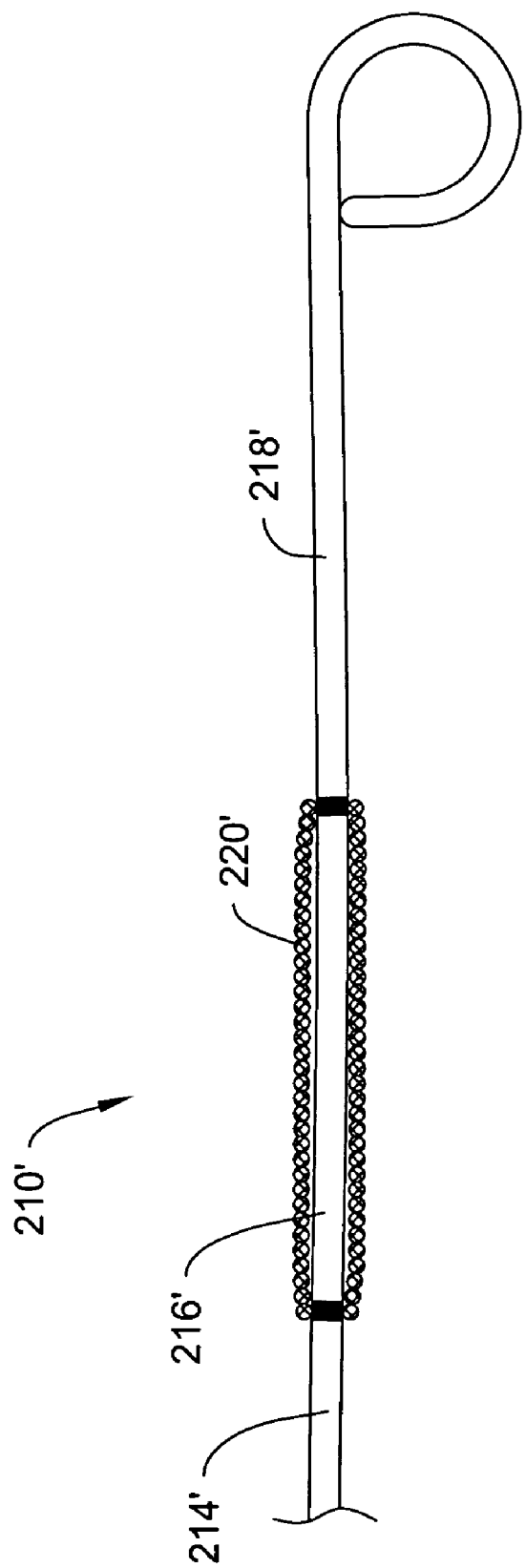
FIG. 5A is a side view of another example medical device.

Actuating member 220 in FIG. 5 can be configured to bias actuating shaft portion 216 in either an elongated or shortened configuration. For example, the outwardly-bowed shape of actuating members 220 may exert a spring force onto actuating shaft portion that tends to bias actuating shaft portion 216 into the shortened configuration. As actuating shaft portion 216 shifts from the shortened configuration to the elongated configuration, actuating members 220 may tend to elongate and/or otherwise move toward and become more closely associated with actuating shaft portion 216 (like how actuating members 220' are shown in FIG. 5A). It should be understood, however, in other embodiments, the actuator member 220 may be configured to bias the shaft portion 216 into an elongated configuration and/or into a curved configuration.

FIG. 5A is another example device 210' (or another configuration of device 510) including proximal shaft portion 214', actuating shaft portion 216', and distal shaft portion 218'. Device 210' is similar to device 210, except that actuating members 220' are more closely associated with actuating shaft portion 216'. According to this embodiment, actuating members 220' may exert a spring force onto actuating shaft portion 216' that tends to bias actuating shaft portion 216' into the elongated configuration. When actuating shaft portion 216' shifts to the shortened configuration, actuating members 520' may tend to bow outwardly (like how actuating members 220 bow outward in FIG. 5). It should be understood, however, in other embodiments, the actuator member 220' may be configured to bias the shaft portion 216' into a shortened configuration and/or into a curved configuration.

Figure 6:
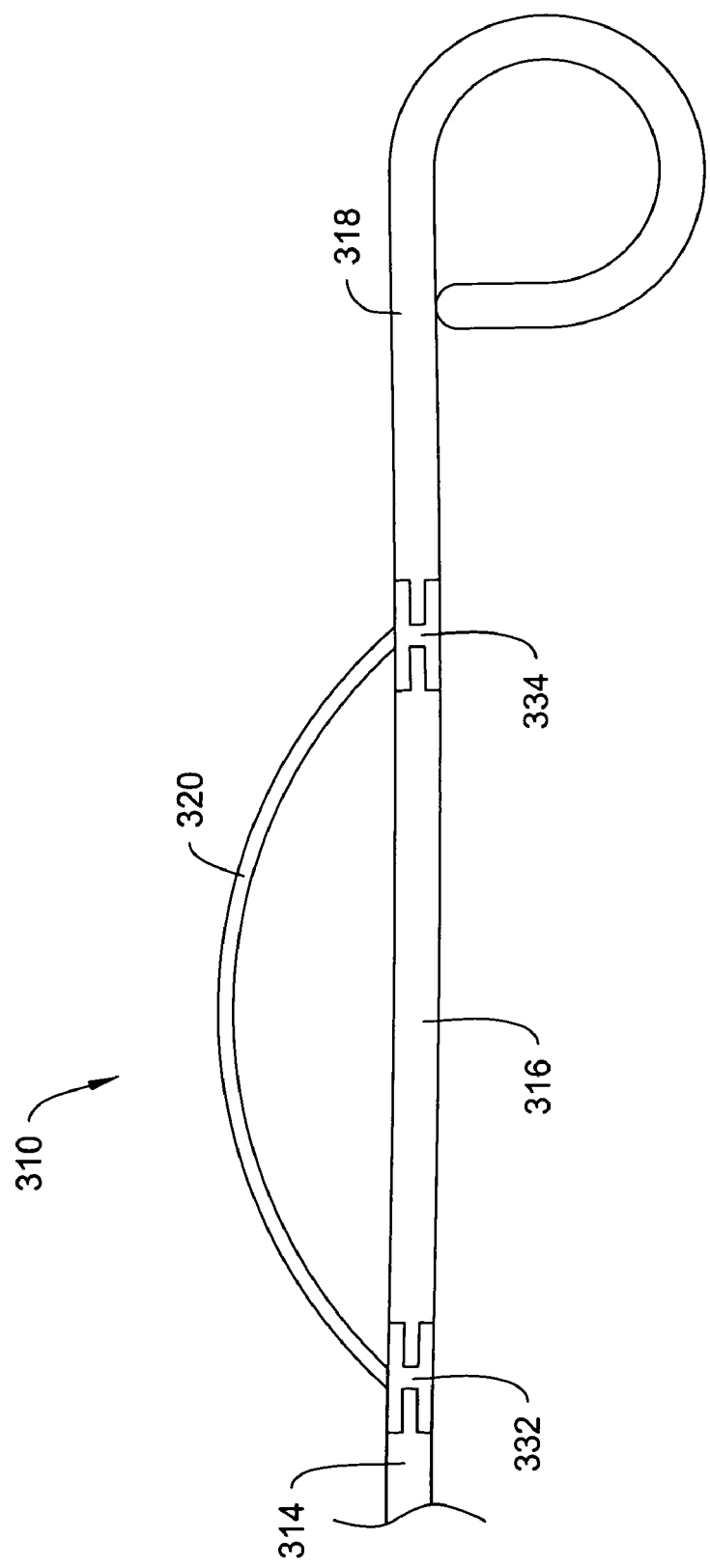
FIG. 6 is a side view of another example medical device.

FIG. 6 illustrates another example actuating device 310 that is similar to any of the other devices disclosed herein except that only a singular non-coiled actuating member 320 is utilized and that a set of mechanical connectors 332/334 are utilized to connect proximal shaft portion 314 to actuating shaft portion 316 and to connect actuating shaft portion 316 to distal shaft portion 318. Connectors 332/334 may be configured to fit over the ends of the relevant portions to secure the portions together. In some embodiments, connectors 332/334 may also be adhesively bonded, thermally bonded, welded, etc. to the opposing portions. According to this embodiment, it may be desirable to manufacture connectors 332/334 from a material that is compatible for welding to differing materials. For example, connectors 332/334 may be made from an inconel alloy such as inconel 825, which is compatible for welding to both stainless steel and nitinol. Some other examples of suitable techniques and structures that can be used for connectors 332/334 are disclosed in U.S. patent application Ser. Nos. 09/972,276 filed on Oct. 5, 2001; and 10/086,992 filed on Feb. 28, 2002, the entire disclosures of which are herein incorporated by reference.

Figure 7:
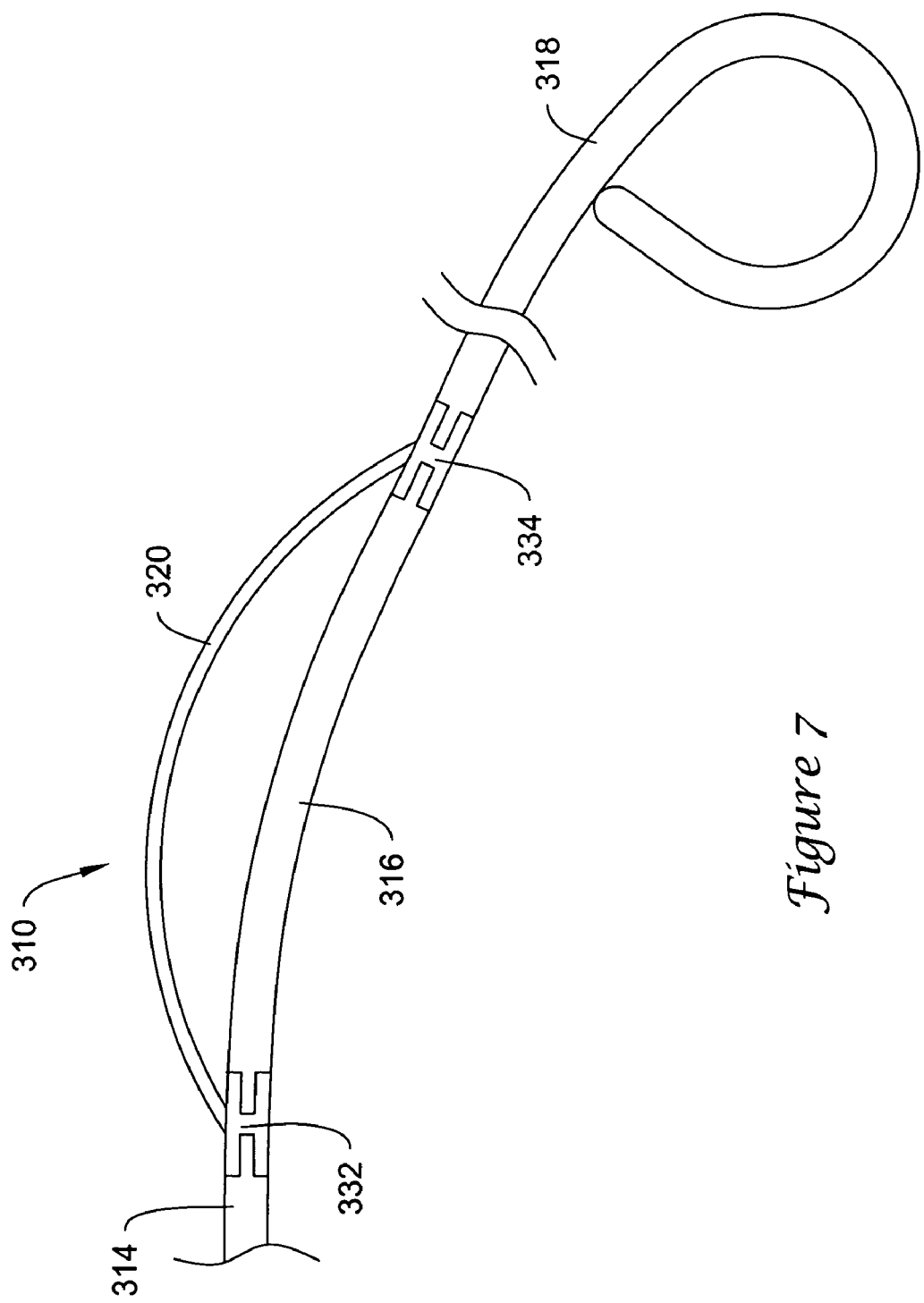
FIG. 7 is a side view of the device shown in FIG. 6, where the actuating shaft is in an alternative shape configuration.

Activation of device 310 can cause actuating shaft portion 316 to return to its previously set austenitic shape. As described above, this can be essentially any shape. For example, FIG. 7 illustrates device 310 where the previously set shape could be curved. According to this embodiment, actuating shaft portion 316 is adapted to shift from a generally straightened martensite configuration (FIG. 6) to a curved austenite configuration (FIG. 7). Alternatively, the previously set shape could be the straightened configuration (FIG. 6) that can be shifted to from the curved configuration (FIG. 7). According to this embodiment, actuation member 320 may be configured to bias actuating shaft portion 316 into the curved configuration. In some other embodiments, actuation portion 316 may have two-way shape memory as described above so that different thermal conditions can cause actuating shaft portion 316 to shift to either the straightened or curved configuration upon activation. For example, one set of thermal conditions may cause actuating shaft portion 316 to shift into one configuration and another set of thermal conditions may cause actuating shaft portion 316 to shift into another configuration. In can be appreciated that if actuating shaft portion 316 (or any other actuating shaft portion described herein) has two-way shape memory then actuating members 320 may not be necessary.

The ability to selectively curve or straighten device 310 may be desirable for a number of reasons. For example, selectively curving or straightening may aid in navigation. This is because when advancing device 310 through the tortuous vasculature, a number of curves or bends may be encountered. It may be more difficult for a straightened (or curved) medical device to navigate the bends, especially those that a particularly tight. The ability to selectively curve or straighten device 310 may allow a user to more easily pass device 310 through these bends.

Figure 8:
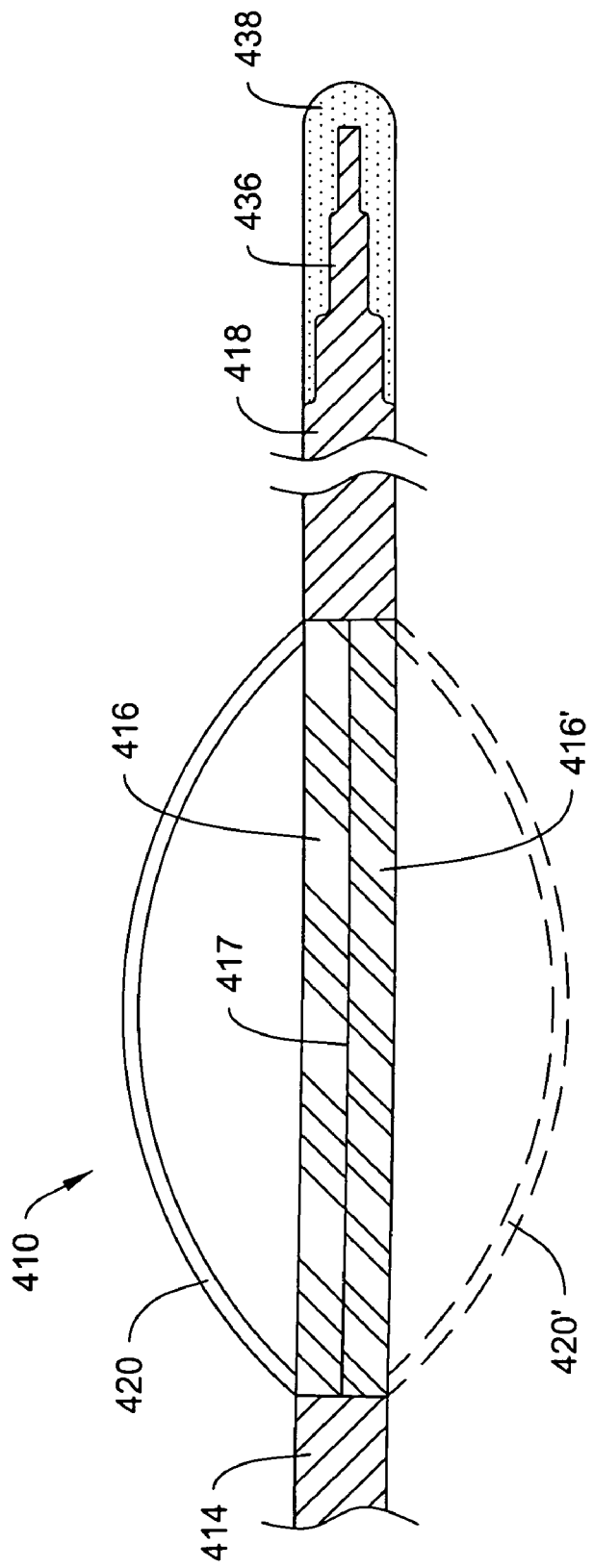
FIG. 8 is a side view of another example medical device.
Figure 9:
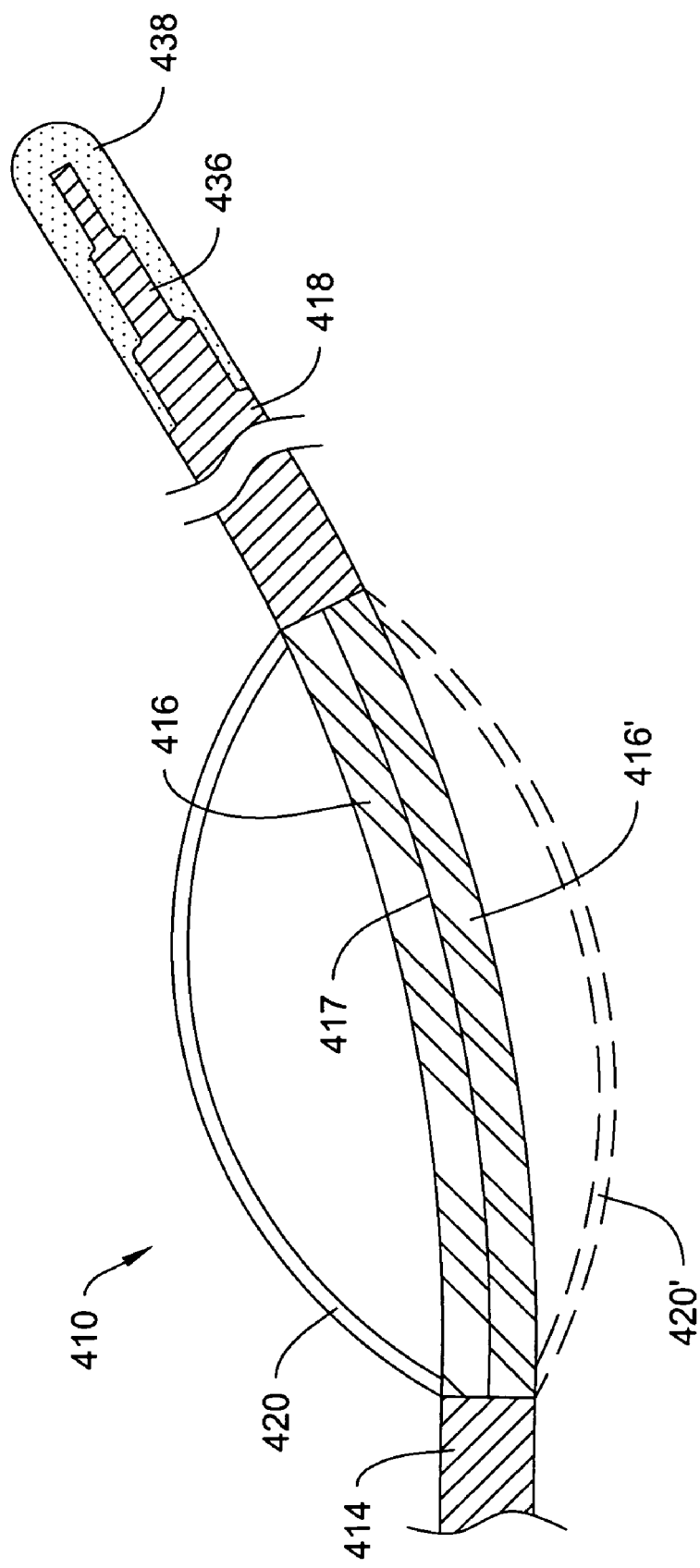
FIG. 9 is a side view of the device shown in FIG. 8, where the actuating shaft is in an alternative shape configuration.

FIG. 8 illustrates another example device 410 that is similar to other devices disclosed herein except that the actuating shaft portion includes a plurality of sections, depicted as portion 416 and 416'. An insulator material or layer 417 may be disposed between portions 416/416'. Insulator 417 may function by substantially preventing heat from dissipating directly from portion 416 to 416'. Insulator 417 may be made from any suitable material including any of those disclosed herein. In some embodiments, actuating shaft portions 416/416' may be made from the same or similar material. For example, portions 416/416' may both be made from nitinol, but they may have different activation temperatures and/or be set to different shapes. This feature allows device 410 to curve in one direction (e.g., by activating actuation portion 416 as seen in FIG. 9) when heated to a first temperature as well as curve device 410 in a different direction (e.g., by activating actuation portion 416') when heated to another temperature. Alternatively, activating actuation portion 416 may curve device 410 to a certain extent (i.e., curve to a certain angle) and activating actuation portion 416' may curve device 410 to a greater extent. In still other embodiments, activation may cause a curved device 410 to become straightened by activating portion 416 and then curved (in either the previously curved direction or another direction) by activating portion 416'. This feature allows device 410 to be selectively straightened as well as be selectively curved. Again, this feature may desirably impact the navigation characteristics and/or trackability of devices such as device 410. Actuation member 420 (or "members" as shown in FIG. 8 by a phantom drawn second actuation member 420') may bias actuation portion 416 or portions 416/416' into one configuration such as a straightened configuration or a curved configuration. In other embodiments, actuation members 420 may not be necessary because the desired shape can be achieved by activating different portions 416/416'.

In some other embodiments, only one of portions 416/416' may be made from a shape memory material. This feature may allow for more selective curving or straightening of device 410. In addition, one or both of portions 416/416' may be plated, laminated, or coated with a shape memory or insulating material to enhance the ability of portions 416/416' to be selectively activated. It should be noted that although FIGS. 8 and 9 shown just two actuating shaft portions 416/416', this is not intended to be limiting because any suitable number of actuating shaft portions may be used without departing from the spirit of the invention.

Device 410 may include a number of the other structural elements seen in the previously-disclosed embodiments. For example, device 410 may include proximal shaft portion 414 and distal shaft portion 418. FIGS. 8 and 9 also illustrate that distal shaft portion 418 may have some of the distal structural characteristics of a polymer tip guidewire. For example, distal shaft portion 418 may include a tapered core section 436 and a polymer coating 438 disposed thereover. The configuration of the polymer tip may vary as seen in the guidewire art. Other embodiments may include, for example, a spring tip construction.

Figure 10:
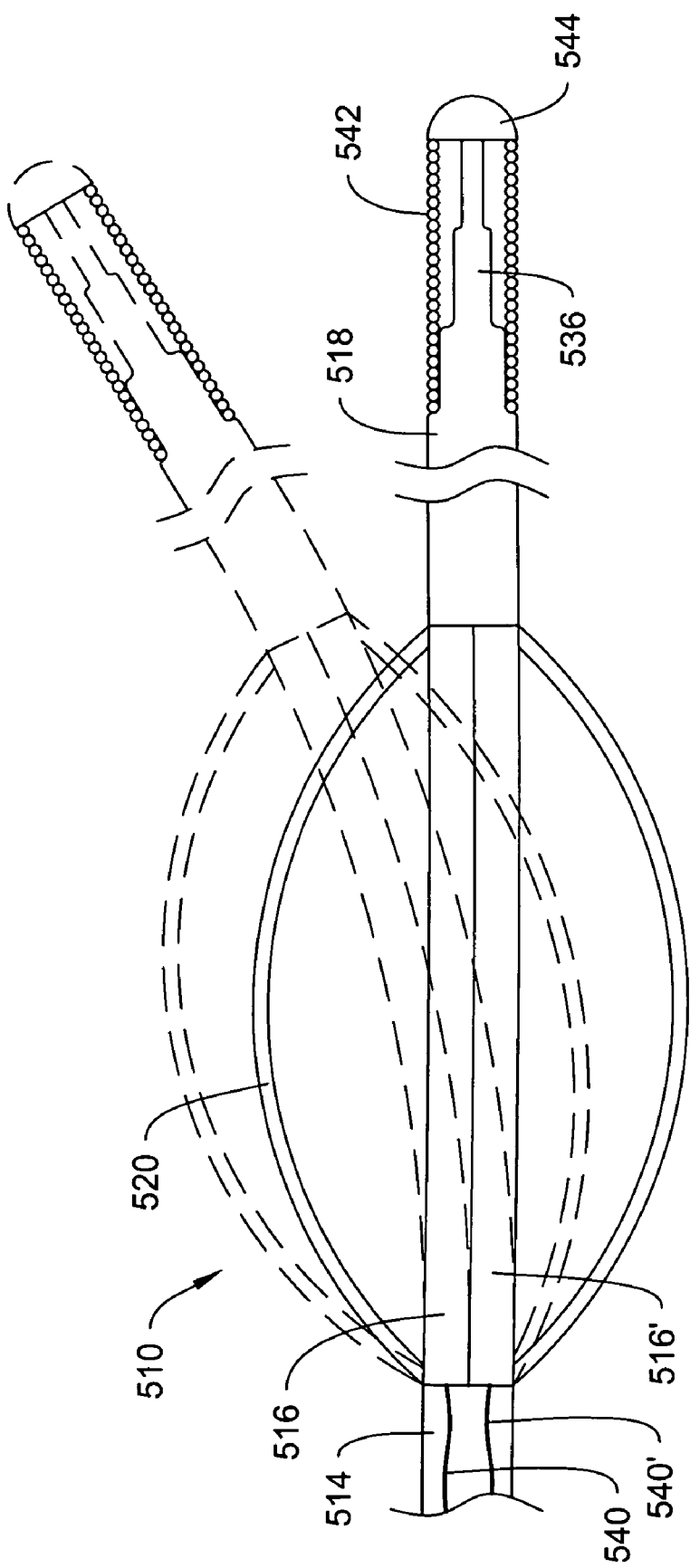
FIG. 10 is a side view of another example medical device.

FIG. 10 illustrates another example device 510 that is similar to any of the other devices disclosed herein except that actuating shaft portions 516/516' each have a conductive lead 540/540' attached thereto and extending proximal therefrom along proximal shaft portion 514. Lead 540/540' may be a conductive wire or strip that is disposed along proximal shaft portion 514, laminated or coated along proximal shaft portion 514, or disposed in any other suitable configuration. According to any of these embodiments, actuating shaft portions 516/516' may each include a shape memory material that can be selectively activated, for example, by passing energy (e.g., current that heats sections 516/516') through leads 540/540' into portion 516 and/or 516'. As described above in relation to FIGS. 8 and 9, actuating shaft portions 516/516' may be set to different shapes so that activating one of portions 516/516' places device 510 into one shape and activating the other portion places device 510 into another. For example, the different shapes may be straightened, curved (to a different extent or in a different direction), and the like, or any other suitable configuration. The shift between a straightened configuration and a curved configuration is shown in FIG. 10 by the curved configuration being depicted in phantom.

Also seen in FIG. 10 is that distal shaft portion 518 may also vary. For example, distal shaft portion 518 may include the structural characteristics of a typical guidewire spring tip. According to this embodiment, distal shaft portion may include tapered section 536, a coil spring 542, and a distal end 544 that may be, for example, a solder ball. It can be appreciated that a plethora of variations may be made to distal shaft portion 518 without departing from the spirit of the invention. Other embodiments may include other alternative tip configurations, for example, polymer tip constructions.

Figure 11:
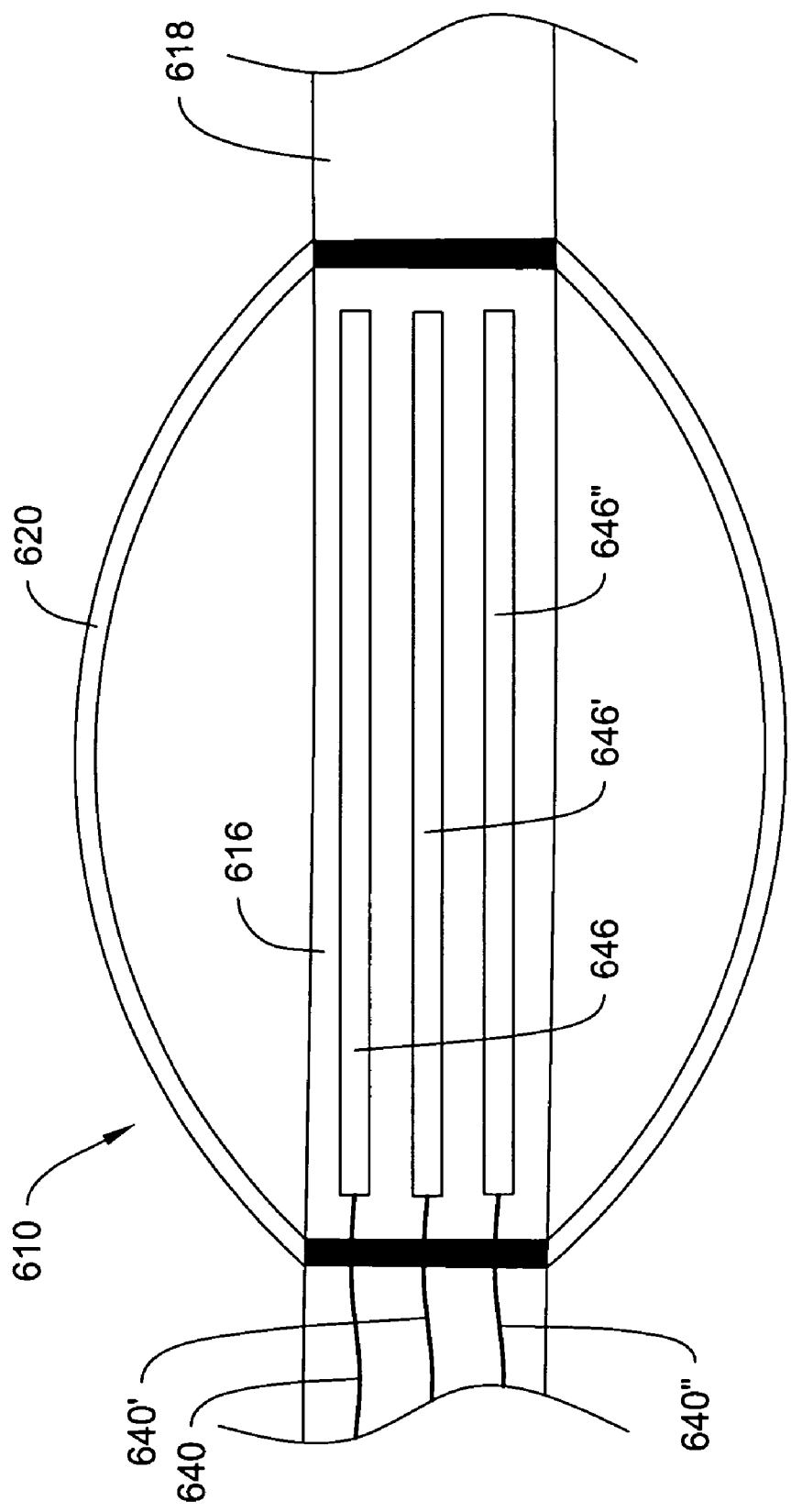
FIG. 11 is a side view of another example medical device.

FIG. 11 illustrates another example portion of a medical device 610 that is similar to any of the other devices disclosed herein except that leads 640/640'/640" extend along proximal shaft portion 614 and terminate in connectors 646/646'/646" that are connected to actuating shaft portion 616. This feature allows a user to selectively activate a section or region of actuating shaft portion 616. The different regions of actuating shaft portion 616 may include a shape memory material and may respond differently to activation so that activating one region via connector 646 results in first response (e.g., curving in a first direction or straightening) an activating another region via connector 646' results in a different response (e.g., curving in a different direction or straightening). Device 610 may also include distal shaft portion 618 that is substantially similar to any of the distal shaft portions described herein.

Although the above discussion has been primarily directed to medical devices that are guidewires, this is not intended to be limiting. Any of the features or characteristics of above embodiments may be utilized for other medical devices such as catheters (e.g., therapeutic, diagnostic, or guide catheters), endoscopic devices, laproscopic devices, embolic protection devices, rotational devices, atherectomy devices, any device designed to pass through an opening or body lumen, and the like, or any other suitable device.

Figure 12:
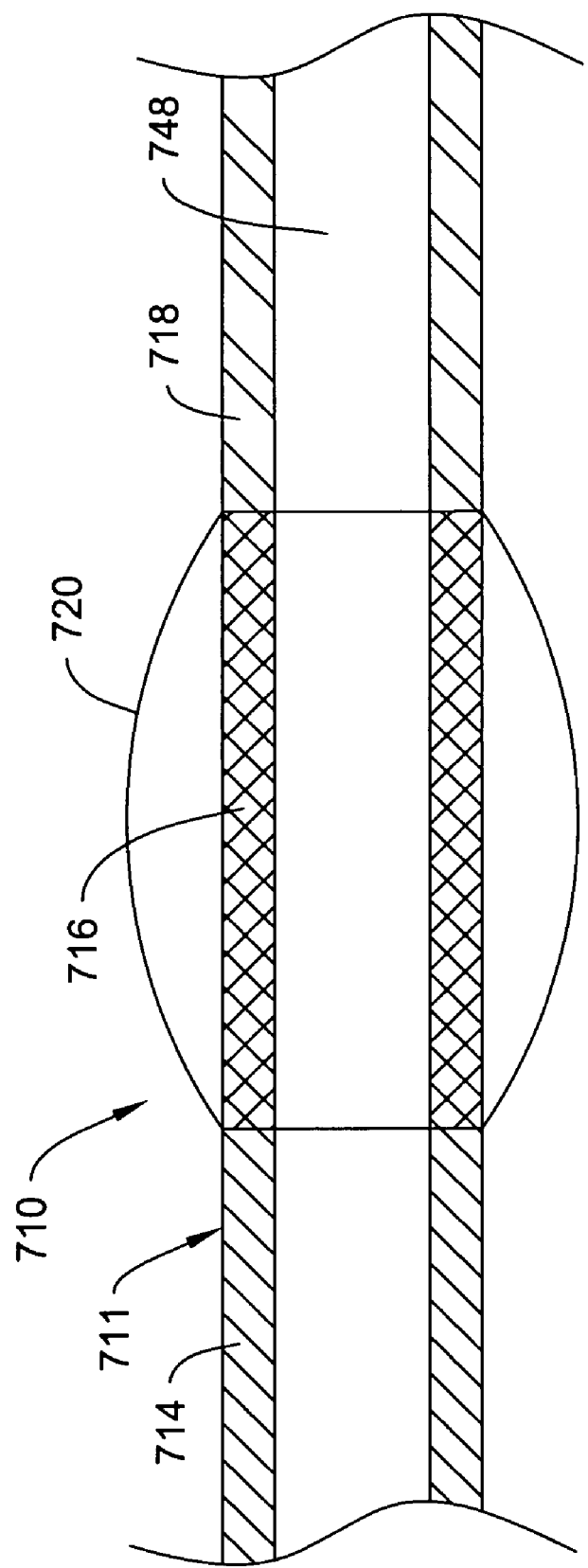
FIG. 12 is a partial cross-sectional side view of another example medical device.

FIG. 12 depicts one example of medical device 710, that is depicted as a catheter including a catheter shaft 711. Catheter shaft 711 may include a lumen 748 defined therein that functions, for example, as a guidewire lumen. Like the other devices described herein, device 710 includes proximal shaft portion 714, actuating shaft portion 716, distal shaft portion 718, and one or more actuating members 720. Actuating shaft portion 716 includes a shape memory material and is adapted to shift between a first configuration and a second configuration. Just like in the above examples, the first and second configurations may be a generally elongated configuration, a generally shortened configuration, a generally straightened configuration, a generally curved configuration, or the like. Actuating members 720 are configured to bias actuating shaft member 716 into one of the configurations—e.g., the first configuration. Upon activation (e.g., via electrical stimulation that heats actuating shaft portion 716 or any other suitable means), actuating shaft portion 716 shifts to the second configuration. Accordingly, activation of actuating shaft portion 716 may cause it to elongate, shorten, straighten, or curve just like any of the aforementioned devices.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A medical device, comprising:
   an elongate shaft including:
      a proximal shaft portion having a proximal end and a distal end,
      a distal shaft portion having a proximal end and a distal end,
      an actuating shaft portion having a proximal end and a distal end, wherein the distal end of the actuating shaft portion is attached to the proximal end of the distal shaft portion and wherein the proximal end of the actuating shaft portion is attached to the distal end of the proximal shaft portion, and
      wherein the actuating shaft portion includes a shape memory material and is configured to shift from a first configuration to a second configuration;
   an actuating member free of a shape memory material disposed on the shaft adjacent the actuating shaft portion, the actuating member being configured to bias the actuating shaft portion into the first or second configuration; and
   one or more electrically conductive leads attached to the actuating shaft portion, the one or more leads being configured to selectively activate a region of the actuating shaft portion.

2. The medical device of claim 1, wherein the elongate shaft is a guidewire.

3. The medical device of claim 1, wherein the proximal shaft portion is a guidewire.

4. The medical device of claim 1, wherein the actuating shaft portion includes nickel-titanium alloy.

5. The medical device of claim 1, wherein the actuating shaft portion includes a first section including a shape memory material and a second section made from a different material.

6. The medical device of claim 5, further comprising an electrically conducting lead attached to the first section and extending proximally therefrom.

7. The medical device of claim 1, wherein the actuating shaft portion includes a first section including a shape memory material, a second section including a shape memory material, and an insulator disposed therebetween.

8. The medical device of claim 7, further comprising an electrically conducting lead attached to the first section and extending proximally therefrom.

9. The medical device of claim 8, further comprising a second electrically conducting lead attached to the second section and extending proximally therefrom.

10. The medical device of claim 1, wherein the elongate shaft is a catheter.

11. The medical device of claim 1, wherein the first configuration is an elongated configuration and wherein the second configuration is a shortened configuration.

12. The medical device of claim 1, wherein the first configuration is a shortened configuration and wherein the second configuration is an elongated configuration.

13. The medical device of claim 1, wherein the first configuration is a curved configuration and wherein the second configuration is a substantially straightened configuration.

14. The medical device of claim 1, wherein the first configuration is a substantially straightened configuration and wherein the second configuration is a curved configuration.

15. The medical device of claim 1, wherein the actuating member includes a coil.

16. The medical device of claim 1, wherein the actuating shaft portion includes a coil.

17. The medical device of claim 1, wherein the distal shaft portion includes a distal ring.

18. The medical device of claim 1, further comprising means for shifting the actuating shaft portion between the first and second configurations.

19. A medical device, comprising:
a proximal shaft portion having a distal end region;
a shape memory shaft portion having a proximal end region attached to the distal end region of the proximal shaft portion and having a distal end region, the shape memory shaft portion being adapted to shift between a first configuration and a second configuration;
an actuating member free of a shape memory material having a first end coupled to the proximal end region of the shape memory shaft and having a second end coupled to the distal end region of the shape memory shaft;
wherein the actuating members are configured to bias the shape memory shaft into the first configuration;
a distal shaft portion having a proximal end region attached to the distal end region of the shape memory shaft portion and having a distal end region, the distal shaft portion including a distal ring; and
one or more electrically conductive leads attached to the shape memory shaft portion, the one or more leads being configured to selectively activate a region of the shape memory shaft portion so that the activated region of the shape memory shaft portion shifts from the first configuration to the second configuration.

20. The medical device of claim 19, wherein the proximal shaft portion, shape memory shaft portion, and distal shaft portion define a guidewire.

21. The medical device of claim 19, wherein the proximal shaft portion, shape memory shaft portion, and distal shaft portion define a catheter.

22. The medical device of claim 19, wherein the shape memory shaft portion includes nickel-titanium alloy.

23. The medical device of claim 19, wherein the shape memory shaft portion includes a first section including a shape memory material and a second section made from a different material.

24. The medical device of claim 23, further comprising an electrically conducting lead attached to the first section and extending proximally therefrom.

25. The medical device of claim 19, wherein the shape memory shaft portion includes a first section including a shape memory material, a second section including a shape memory material, and an insulator disposed therebetween.

26. The medical device of claim 25, further comprising an electrically conducting lead attached to the first section and extending proximally therefrom.

27. The medical device of claim 26, further comprising a second electrically conducting lead attached to the second section and extending proximally therefrom.

28. The medical device of claim 19, further comprising means for shifting the shape memory shaft from the first configuration to the second configuration.

29. The medical device of claim 19, wherein the first configuration is an elongated configuration and wherein the second configuration is a shortened configuration.

30. The medical device of claim 19, wherein the first configuration is a shortened configuration and wherein the second configuration is an elongated configuration.

31. The medical device of claim 19, wherein the first configuration is a curved configuration and wherein the second configuration is a substantially straightened configuration.

32. The medical device of claim 19, wherein the first configuration is a substantially straightened configuration and wherein the second configuration is a curved configuration.

33. The medical device of claim 19, wherein the actuating members include a coil.

34. The medical device of claim 19, wherein the shape memory shaft portion includes a coil.

* * * * *